United States Patent
Jegham et al.

(10) Patent No.: US 6,255,319 B1
(45) Date of Patent: Jul. 3, 2001

(54) 5-ARYL-3-(8-AZABICYCLO[3.2.1]OCT-3-YL)-1,3,4-OXADIAZOL-2(3H)-ONE DERIVATIVES AS 5-HT4 RECEPTOR LIGANDS

(75) Inventors: Samir Jegham, Argenteuil; Alistair Lochead, Charenton; Frédéric Galli, Vaucresson; Alain Nedelec, Colombes; Axelle Samson, Paris; Thierry Gallet, Palaiseau, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/403,003
(22) PCT Filed: Apr. 15, 1998
(86) PCT No.: PCT/FR98/00754
§ 371 Date: Oct. 15, 1999
§ 102(e) Date: Oct. 15, 1999
(87) PCT Pub. No.: WO98/47898
PCT Pub. Date: Oct. 29, 1998

(30) Foreign Application Priority Data
Apr. 18, 1997 (FR) .................................................. 97 04802

(51) Int. Cl.⁷ ......................... A61K 31/46; C07D 451/04
(52) U.S. Cl. ................................ 514/304; 46/125; 46/126
(58) Field of Search ..................................... 546/125, 126; 514/304

(56) References Cited
FOREIGN PATENT DOCUMENTS
WO 97/17345 * 5/1997 (WO) .

* cited by examiner

Primary Examiner—Richard L. Raymond
(74) Attorney, Agent, or Firm—Jacobson Holman PLLC

(57) ABSTRACT

Compound of general formula (I)

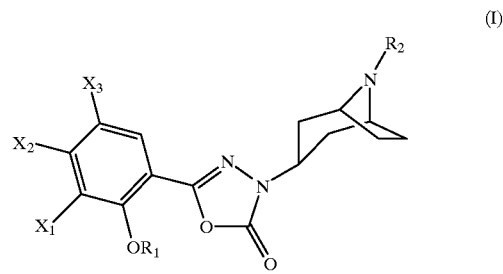

in which $R_1$ represents an alkyl or cycloalkylmethyl group, $X_1$ represents a hydrogen or halogen atom or an alkoxy group, or alternatively $OR_1$ and $X_1$ together represent an $-OCH_2O-$, $-O(CH_2)_2-$, $-O(CH_2)_3-$, $-O(CH_2)_2O-$ or $-(CH_2)_3O-$ group, $X_2$ represents a hydrogen atom or an amino group, $X_3$ represents a hydrogen or halogen atom, and $R_2$ represents a hydrogen atom, an optionally substituted alkyl group, an optionally substituted phenylalkyl group or a group $-(CH_2)_nCO-Z$ in which n represents a number from 1 to 6 and Z represents a 1-piperidyl group. Therapeutic application.

10 Claims, No Drawings

5-ARYL-3-(8-AZABICYCLO[3.2.1]OCT-3-YL)-1,3,4-OXADIAZOL-2(3H)-ONE DERIVATIVES AS 5-HT4 RECEPTOR LIGANDS

The present application is a 371 of PCT/FR98/00754, filed Apr. 19, 1998.

The present invention relates to compounds corresponding to the general formula (I)

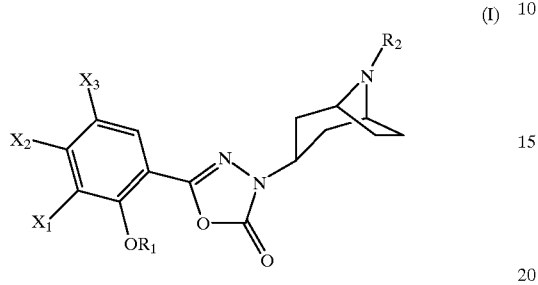

(I)

in which
- $R_1$ represents a $(C_1-C_4)$alkyl or $(C_3-C_7)$cycloalkylmethyl group,
- $X_1$ represents a hydrogen or halogen atom or a $(C_1-C_4)$ alkoxy group, or alternatively
- $OR_1$ and $X_1$ together represent a group of formula —OCH$_2$O—, —O(CH$_2$)$_2$—, —O(CH$_2$)$_3$—, —O(CH$_2$)$_2$O— or —(CH$_2$)$_3$O—,
- $X_2$ represents a hydrogen atom or an amino group,
- $X_3$ represents a hydrogen or halogen atom, and
- $R_2$ represents a hydrogen atom, $(C_1-C_6)$alkyl group, a phenyl$(C_1-C_4)$alkyl group, or a group of general formula —(CH$_2$)$_n$CO—Z in which n represents a number from 1 to 6 and Z represents a 1-piperidyl or 4-(dimethylamino)-1-piperidyl group.

When $R_2$ represents an alkyl group, such a group is preferably a butyl group.

When $R_2$ represents a phenyl$(C_1-C_3)$alkyl group such a group is preferably a 2-phenylethyl group.

When $R_2$ represents a group of general formula —(CH$_2$)$_n$CO—Z, such a group is preferably a 4-[4-(dimethylamino)-1-piperidyl]-4-oxobutyl group, a 5-[4-(dimethylamino)-1-piperidyl]-5-oxopentyl group or a 6-[4-(dimethylamino)-1-piperidyl]-6-oxohexyl group.

The compounds of the invention can exist in the form of free bases or of pharmaceutically acceptable addition salts with acids. On account of the tropane ring, they can also be in the form of endo or exo isomers. Moreover, certain substituents $R_2$ can contain an asymmetric carbon atom; the compounds can thus exist in various pure or mixed geometrical and/or optical isomer forms.

N-(8-azabicyclo[3.2.1]oct-3-yl) benzamides having a structure nearly similar to that of the compounds of the invention and having affinities for the 5-HT$_3$ and 5-HT$_4$ receptors, are disclosed in patent application EP-0554794.

In accordance with the invention, the compounds of general formula (I) can be prepared by a process illustrated by the scheme which follows.

An ester of general formula (II), in which $R_1$, $X_1$, $X_2$ and $X_3$ are as defined above and $R_3$ represents a methyl or ethyl group, is reacted with hydrazine hydrate, in the absence of solvent or in a polar protic solvent, for example ethanol, in order to obtain a hydrazide of general formula (III) which is cyclized into the oxadiazole of general formula (IV) either by means of phosgene, in an aprotic solvent, for example dioxane, or by means of phenyl chloroformate, in an aprotic solvent, for example toluene.

Scheme

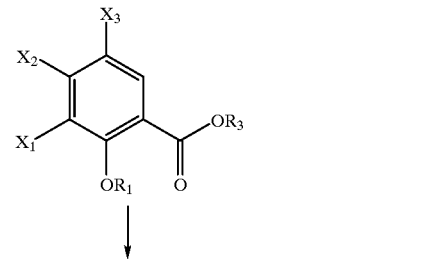
(II)

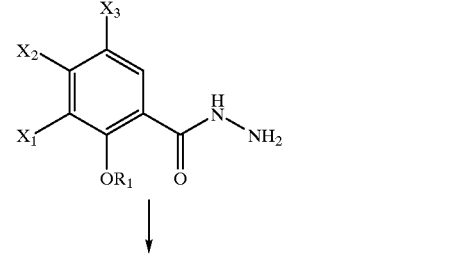
(III)

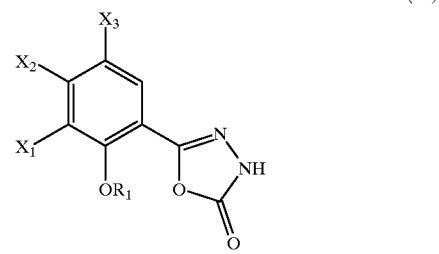
(IV)

(V)

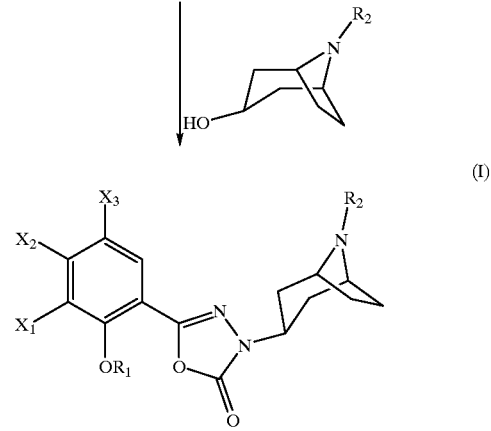
(I)

The oxadiazole of general formula (IV) is then reacted with a tropanol of general formula (V), in which $R_2$ is as defined with respect to the general formula (I), but is other than a hydrogen atom, or alternatively represents a (1,1-dimethylethoxy)carbonyl protecting group, in the presence of triphenylphosphine and ethyl azodicarboxylate, in an aprotic solvent, for example tetrahydrofuran, after which, if necessary, the nitrogen of the tropane ring is deprotected by means of trifluoroacetic acid in order to obtain a compound of general formula (I) in which $R_2$ represents a hydrogen atom and, if so desired, the compound obtained is reacted with a derivative of general formula $R_2$—X, in which X represents a leaving group, for example a halogen atom or a methanesulphonate or para-toluenesulphonate group, and $R_2$ is as defined with respect to the general formula (I), but is other than a hydrogen atom, in the presence of triethylamine, in an aprotic solvent, for example acetonitrile. The starting esters of general formula (II) and/or the corresponding acids are described in particular in patent applications EP-0,231,139, EP-0,234,872, WO-84/03281, WO-93/16072 and WO-94/19344.

The tropanols of general formula (V) are known or can be prepared according to any known methods. 8-[(1,1-Dimethylethoxy)carbonyl]-8-azabicyclo[3.2.]octan-3-ol can be prepared by the method described in *Drug Metabolism and Disposition* (1992) 20(4) 596–602.

The examples which follow illustrate in detail the preparation of a few compounds according to the invention. The elemental microanalyses and the IR and NMR spectra confirm the structures of the compounds obtained. The compound numbers given in parentheses in the titles correspond to those in the table given later. In the compound names, the hyphen "-" forms part of the word, and the line "_" serves merely to indicate a line break; it should be removed if no line break is present, and should not be replaced either by a normal hyphen or by a space.

EXAMPLE 1

Compound No. 1

5-(4-Amino-5-chloro-2-methoxyphenyl)-3-(8-methyl-8-azabicyclo[3.2.1]oct-3-yl)-1,3,4-oxadiazol-2(3H)-one.

1.1. 4-Amino-5-chloro-2-methoxybenzoic acid hydrazide 51.5 g (0.239 mol) of methyl 4-amino-5-chloro-2-methoxybenzoate suspended in 460 ml of ethanol are introduced into a 1 l reactor. 119 g (2.39 mol) of hydrazine hydrate are added, over 15 min, and the mixture is refluxed for 15 h.

The mixture is cooled using an ice bath and the precipitate is filtered off, rinsed with ethanol and dried under reduced pressure at 80° C. for 2 h 30.

47.5 g of product are thus obtained.
Melting point: 211° C.

1.2. Phenylmethyl [2-chloro-5-methoxy-4-(5-oxo-4,5-dihydro-1,3,4-oxadiazol-2-yl)phenyl]carbamate 461 ml (0.875 mol) of a 1.93M solution of phosgene in toluene are added dropwise, over one hour, at room temperature and with magnetic stirring, to a suspension of 37.7 g (0.175 mol) of 4-amino-5-chloro-2-methoxybenzoic acid hydrazide in 1200 ml of dioxane in a 3 l reactor.

The mixture is stirred at room temperature overnight and is then heated at 80° C. for 1 h. The excess phosgene is stripped off by passing a stream of argon through at this temperature for 2 h. 72 ml (0.7 mol) of benzyl alcohol are then added and heating is continued for 1 h at 100° C. The mixture is cooled and concentrated under reduced pressure, and the residue is triturated from isopropyl ether. The solid obtained is filtered off and dried. 60.3 g of product are thus obtained.

Melting point: 214° C.

1.3. Phenylmethyl [2-chloro-4-[4-(8-methyl-8-azabicyclo[3.2.1]oct-3-yl)-5-oxo-4,5-dihydro-1,3,4-oxadiazol-2-yl]-5-methoxyphenyl]carbamate hydrochloride 1 g (2.66 mmol) of phenylmethyl [2-chloro-5-methoxy-4-(5-oxo-4,5-dihydro-1,3,4-oxadiazol-2-yl)phenyl] carbamate, 0.47 g (3.33 mmol) of endo-8-methyl-8-azabicyclo[3.2.1]octan-3-ol and 1.05 g (4 mmol) of triphenylphosphine dissolved in 15 ml of tetrahydrofuran are introduced into a 50 ml three-necked round-bottomed flask, the mixture is cooled to 0° C., 0.63 ml, i.e. 0.70 g (4 mmol), of ethyl azodicarboxylate is added and the mixture is stirred at 40° C. for 3 h 30.

The solvent is evaporated off under reduced pressure, the residue is taken up in 15 ml of a mixture of diethyl ether and diisopropyl ether and the solid is collected by filtration. After rinsing and drying, 1.6 g of solid are obtained. The hydrochloride of this is prepared in a conventional manner and is triturated from acetone and recrystallized from ethanol. 2.22 g of salt are obtained.

1.4. 5-(4-Amino-5-chloro-2-methoxyphenyl)-3-(8-methyl-8-azabicyclo[3.2.1]oct-3-yl)-1,3,4-oxadiazol-2(3H)-one 0.94 g (1.76 mmol) of phenylmethyl [2-chloro-4-[4-(8-methyl-8-azabicyclo[3.2.1]oct-3-yl)-5-oxo-4,5-dihydro-1,3,4-oxadiazol-2-yl]-5-methoxyphenyl]carbamate hydrochloride is introduced into a three-necked round-bottomed flask containing 17 ml of acetic acid, 3.12 ml of 33% hydrobromic acid in acetic acid (i.e. 7 equivalents of hydrobromic acid) are added and the medium is stirred for 24 h.

20 ml of diethyl ether are added, the solid is collected by filtration, rinsed with diethyl ether and taken up in water, aqueous ammonia is added to basic pH and a very fine precipitate is obtained, which is collected by filtration. After drying, 0.45 g of compound is isolated.

Melting point: 208° C.

EXAMPLE 2

Compound No. 3

5-(8-Amino-7-chloro-2,3-dihydro-1,4-benzodioxin-5-yl)-3-(8-azabicyclo[3.2.1]oct-3-yl)-1,3,4-oxadiazol-2(3H)-one hydrochloride

2.1. Phenylmethyl [6-chloro-8-[4-[8-[(1,1-dimethyl_ethoxy)carbonyl]-8-azabicyclo[3.2.1]oct-3-yl]-5-oxo-4,5-dihydro-1,3,4-oxadiazol-2-yl]-2,3-dihydro-1,4-benzodioxin-5-yl)carbamate 7.1 g (0.030 mol) of phenylmethyl endo-8-[(1,1-dimethylethoxy)carbonyl]-8-azabicyclo[3.2.1]octan-3-ol, 10 g (0.025 mol) of phenylmethyl [6-chloro-8-(5-oxo-4,5-dihydro-1,3,4-oxadiazol-2-yl)2,3-dihydro-1,4-benzodioxin-5-yl)carbamate (prepared from the corresponding methyl benzoate according to the method described in steps 1.1 and 1.2), 8.44 g (0.032 mol) of triphenylphosphine, 5.6 g (0.032 mol) of ethyl azodicarboxylate and 400 ml of dry tetrahydrofuran are introduced into a round-bottomed flask and the mixture is stirred at room temperature overnight. The solvent is evaporated off under reduced pressure and the residue is purified by chromatography on silica gel, eluting with a 50/50 mixture of ethyl acetate and heptane, and 13.0 g of compound are obtained.

Melting point: 210° C.

2.2. Phenylmethyl [6-chloro-8-[4-(8-azabicyclo[3.2.1]oct-3-yl)-5-oxo-4,5-dihydro-1,3,4-oxadiazol-2-yl]-2,3-dihydro-1,4-benzodioxin-5-yl]carbamate 13.75 g (0.022 mol) of phenylmethyl [6-chloro-8-[4-[8-[(1,1-dimethylethoxy)carbonyl]-8-azabicyclo[3.2.1]oct-3- yl]-5-oxo-4,5-dihydro-1,3,4-oxadiazol-2-yl]-2,3-dihydro-1, 4-benzodioxin-5-yl)carbamate dissolved in 150 ml of chloroform are introduced into a 500 ml three-necked round-bottomed flask, 17.05 ml (0.221 mol) of trifluoroacetic acid are added slowly, over 20 min, and the mixture is stirred for 19 h. A further 17.05 ml (0.221 mol) of trifluoroacetic acid are added and the mixture is stirred for 5 h.

The mixture is concentrated and the residue is crystallized from 300 ml of diethyl ether. The solid is taken up in 100 ml of water, 3 ml of 30% sodium hydroxide are added, the mixture is extracted with chloroform and the evaporation residue is triturated from diisopropyl ether. 7.88 g of compound are obtained.

Melting point: 140° C.

2.3. 5-(8-Amino-7-chloro-2,3-dihydro-1,4-benzodioxin-5-yl)-3-(8-azabicyclo[3.2.1]oct-3-yl)-1, 3,4-oxadiazol-2(3H)-one hydrochloride A suspension of 0.88 g (1.72 mmol) of phenylmethyl [6-chloro-8-[4-(8-azabicyclo[3.2.1]oct-3-yl]-5-oxo-4,5-dihydro-1,3,4-oxadiazol-2-yl]-2,3-dihydro-1,4-benzodioxin-5-yl)carbamate in 10 ml of acetic acid is prepared, 2.2 ml of a 33% solution of hydrobromic acid in acetic acid are added and the mixture is stirred overnight. Diethyl ether is added to the mixture, the precipitate is collected by filtration, rinsed with diethyl ether and taken up in water, the solution is washed with ethyl acetate, 0.5 ml of aqueous 30% sodium hydroxide is added, this mixture is extracted four times with chloroform, the organic phase is washed with water, dried over sodium sulphate and filtered and the solvent is evaporated off. The residue is triturated from diethyl ether, drained, taken up in refluxing ethanol and treated with hydrochloric ethanol. 0.61 g of hydrochloride is finally isolated.

Melting point: 210° C.

EXAMPLE 3

Compound No. 5

5-(8-Amino-7-chloro-2,3-dihydro-1,4-benzodioxin-5-yl)-3-(8-butyl-8-azabicyclo[3.2.1]oct-3-yl)-1,3,4-oxadiazol-2(3H)-one hydrobromide 3.1. Phenylmethyl [6-chloro-8-[4-(8-butyl-8-azabicyclo[3.2.1]oct-3-yl)-5-oxo-4,5-dihydro-1,3,4-oxadiazol-2-yl]-2,3-dihydro-1,4-benzodioxin-5-yl) carbamate 1.54 g (3 mmol) of phenylmethyl [6-chloro-8-(8-azabicyclo[3.2.1]oct-3-yl)-5-oxo-4,5-dihydro-1,3,4-oxadiazol-2-yl]-2,3-dihydro-1,4-benzodioxin-5-yl] carbamate and 1.2 g (12 mmol) of triethylamine dissolved in 20 ml of acetonitrile are introduced into a 100 ml three-necked round-bottomed flask, 0.82 g (6 mmol) of 1-bromobutane is added and the mixture is heated at 60° C. for 20 h.

The solvent is evaporated off, the residue is taken up in water and extracted with ethyl acetate, the organic phase is washed with water and dried, the solvent is evaporated off under reduced pressure and the residue is purified by chromatography on silica gel, eluting with a 95/5/0.5 mixture of chloroform, methanol and aqueous ammonia. 1.25 g of compound are obtained.

Melting point: 142° C.

3.2. 5-(8-Amino-7-chloro-2,3-dihydro-1,4-benzodioxin-5-yl)-3-(8-butyl-8-azabicyclo[3.2.1]oct-3-yl)-1,3,4-oxadiazol-2(3H)-one hydrobromide 1.2 g (2.11 mmol) of phenylmethyl [6-chloro-8-[4-(8-butyl-8-azabicyclo[3.2.1]oct-3-yl)-5-oxo-4,5-dihydro-1,3, 4-oxadiazol-2-yl]-2,3-dihydro-1,4-benzodioxin-5-yl] carbamate, 12 ml of acetic acid and 3 ml of 33% hydrobromic acid in acetic acid are introduced into a 50 ml round-bottomed flask and the solution obtained is stirred at room temperature for 18 h.

Diethyl ether is added and the solid is collected by filtration, rinsing with diethyl ether, and is crystallized from 2-propanol. 0.92 g of hydrobromide is obtained, which is triturated from ethanol, and 0.79 g of pure compound is finally isolated.

Melting point: >260° C.

EXAMPLE 4

Compound No. 4

5-(8-Amino-7-chloro-2,3-dihydro-1,4-benzodioxin-5-yl)-3-[8-(2-phenylethyl)-8-azabicyclo[3.2.1]oct-3-yl]-1,3,4-oxadiazol-2(3H)-one 4.1 Phenylmethyl [6-chloro-8-[4-[8-(2-phenylethyl)-8-azabicyclo[3.2.1]oct-3-yl]-5-oxo-4,5-dihydro-1,3, 4-oxadiazol-2-yl]-2,3-dihydro-1,4-benzodioxin-5-yl] carbamate 1.33 g (2.6 mmol) of phenylmethyl [6-chloro-8-[4-(8-azabicyclo[3.2.1]oct-3-yl)-5-oxo-4,5-dihydro-1,3,4-oxadiazol-2-yl]-2,3-dihydro-1,4-benzodioxin-5-yl) carbamate, 1.05 g (10.4 nmol) of triethylamine and 0.96 g (5.2 mmol) of (2-bromoethyl)benzene dissolved in 20 ml of acetonitrile are introduced into a 100 ml three-necked round-bottomed flask and the mixture is heated at 60° C. for 18 h.

A further 0.48 g (2.6 mmol) of (2-bromoethyl)benzene is added and heating is continued for 5 h.

The solvent is evaporated off under reduced pressure, the residue is taken up in water and extracted with chloroform, the organic phase is washed with water and dried, the solvent is evaporated off under reduced pressure and the residue is purified by chromatography on a column of silica gel, eluting with a 99/1/0.1 mixture of chloroform, methanol and aqueous ammonia. 1.28 g of product are obtained which, after crystallization from diisopropyl ether, gives 1.18 g of pure compound.

Melting point: 118° C.

4.2. 5-(8-Amino-7-chloro-2,3-dihydro-1,4-benzodioxin-5-yl)-3-[8-(2-phenylethyl)-8-azabicyclo [3.2.1]oct-3-yl]-1,3,4-oxadiazol-2(3H)-one 1.18 g (1.91 mmol) of phenylmethyl [6-chloro-8 -[4-[8-(2-phenylethyl)-8-azabicyclo[3.2.1]oct-3-yl]-5-oxo-4,5-dihydro-1,3,4-oxadiazol-2-yl]-2,3-dihydro-1,4-benzodioxin-5-yl]carbamate, 12 ml of acetic acid and 2.95 ml of hydrobromic acid dissolved in acetic acid are introduced into a 50 ml round-bottomed flask and the solution is stirred at room temperature for 18 h.

Diethyl ether is added, the precipitate is collected by filtration, rinsing it with diethyl ether, the crude hydrobromide thus obtained is taken up in 13 ml of water and 20 ml of chloroform, 0.5 ml of 30% sodium hydroxide is added, the mixture is extracted with chloroform, the solvent is evaporated off under reduced pressure and the residue is triturated from diisopropyl ether. 0.703 g of pure compound is obtained in the form of the free base.

Melting point: 227° C.

EXAMPLE 5

Compound No. 7

3-(8-Azabicyclo[3.2.1]oct-3-yl)-5-(6-chloro-3,4-dihydro-2H-1-benzopyran-8-yl)-1,3,4-oxadiazol-2 (3H)-one hydrochloride 2.83 g (11.2 mmol) of 5-(6-chloro-3,4-dihydro-2H-1-benzopyran-8-yl)-1,3,4-oxadiazol-2(3H)-one (prepared from the corresponding methyl benzoate according to the method described in steps 1.1 and 1.2), 2.54 g (11.2 mmol) of endo-8-(1,1-dimethylethoxy_ carbonyl)-8-azabicyclo[3.2.1]octan-3-ol and 4.11 g (15.68 mmol) of triphenylphosphine are introduced into 100 ml of tetrahydrofuran, the mixture is cooled to 0° C. under an argon atmosphere, 3.0 ml of ethyl azodicarboxylate are added and the mixture is stirred at room temperature overnight.

The solvent is evaporated off under reduced pressure, the residue is taken up in 100 ml of dichloromethane, 17.3 ml of trifluoroacetic acid are added and the mixture is stirred for 12 h.

The mixture is concentrated to dryness, the residue is taken up in 1 N hydrochloric acid, the mixture is washed with diethyl ether and then with ethyl acetate, potassium carbonate is added to the aqueous phase and the mixture is extracted with chloroform. The aqueous phase is washed and dried, the solvent is evaporated off under reduced pressure, the residue is taken up in 1 equivalent of hydrochloric ethanol, the mixture is concentrated to dryness and the residue is recrystallized from a 9/1 mixture of water and 2-propanol. After filtration and drying, 1.8 g of compound are obtained.

Melting point: 254° C.

EXAMPLE 6

Compound No. 9

3-(8-Butyl-8-azabicyclo[3.2.1]oct-3-yl)-5-(6-chloro-3,4-dihydro-2H-1-benzopyran-8-yl)-1,3,4-oxadiazol-2(3H)-one hydrochloride A mixture of 0.96 g (2.38 mmol) of 3-(8-azabicyclo[3.2.1]oct-3-yl)-5-(6-chloro-3,4-dihydro-2H-1-benzopyran-8-yl)-1,3,4-oxadiazol-2(3H)-one hydrochloride, 0.28 ml, i.e. 0.36 g (2.62 mmol) of bromobutane, 0.72 g (5.24 mmol) of potassium carbonate and 40 ml of acetonitrile is heated at 60° C. for 24 h.

The solvent is evaporated off under reduced pressure, the residue is taken up in water and extracted with chloroform, the aqueous phase is washed and dried, the solvent is evaporated off under reduced pressure and the residue is purified by chromatography on a column of silica, eluting with dichloromethane. The base is taken up in 1 equivalent of hydrochloric ethanol, the solution is concentrated and the salt is recrystallized from 2-propanol, drained and dried. 0.38 g of compound is obtained.

Melting point: 242° C.

EXAMPLE 7

Compound No. 10

3-(8-Azabicyclo[3.2.1]oct-3-yl)-5-(5-chloro-2,3-dihydrobenzofuran-7-yl)-1,3,4-oxadiazol-2(3H)-one hydrochloride 3.58 g (15 mmol) of 5-(5-chloro-2,3-dihydrobenzofuran-7-yl)-1,3,4-oxadiazol-2(3H)-one (prepared from the corresponding methyl benzoate according to the method described in steps 1.1 and 1.2), 3.41 g (15 mmol) of endo-S-(1,1-dimethylethoxycarbonyl)-8-azabicyclo[3.2.1]octan-3-ol and 5.51 g (21 mmol) of triphenylphosphine are introduced into 120 ml of tetrahydrofuran, the mixture is cooled to 0° C. under an argon atmosphere, 4.0 ml, i.e. 4.44 g (25.5 mmol) of ethyl azodicarboxylate are added and the mixture is stirred at room temperature overnight.

The solvent is evaporated off under reduced pressure, the residue is taken up in 150 ml of dichloromethane, 23.1 ml of trifluoroacetic acid are added and the mixture is stirred for 12 h. The mixture is concentrated to dryness, the residue is taken up in 1 N hydrochloric acid, the mixture is washed with diethyl ether and then with ethyl acetate, potassium carbonate is added to the aqueous phase to pH=10 and the mixture is extracted with chloroform. The organic phase is washed and dried, the solvent is evaporated off under reduced pressure, the residue is taken up in 1 equivalent of hydrochloric ethanol, the mixture is concentrated to dryness and the residue is recrystallized from a 49/1 mixture of 2-propanol and water. After filtration and drying, 1.7 g of compound are obtained.

Melting point: >260° C.

EXAMPLE 8

Compound No. 11

3-[8-(2-Phenylethyl)-8-azabicyclo[3.2.1]oct-3-yl]-5-(5-chloro-2,3-dihydrobenzofuran-7-yl)-1,3,4-oxadiazol-2(3H)-one hydrochloride A mixture of 0.80 g (2.08 mmol) of 3-(8-azabicyclo[3.2.1]oct-3-yl)-5-(5-chloro-2,3-dihydrobenzofuran-7-yl)-1,3,4-oxadiazol-2(3H)-one hydrochloride, 0.31 ml, i.e. 0.43 g (2.29 mmol) of (2-bromoethyl)benzene, 0.63 g (4.58 mmol) of potassium carbonate and 30 ml of acetonitrile is heated at 60° C. for 24 h.

The solvent is evaporated off under reduced pressure, the residue is taken up in water and extracted with chloroform, the organic phase is washed and dried, the solvent is evaporated off under reduced pressure and the residue is purified by chromatography on a column of silica gel, eluting with a 98/2 mixture of dichloromethane and ethanol. The base is taken up in 1 equivalent of hydrochloric ethanol, the solution is concentrated and the salt is recrystallized from ethanol, drained and dried. 0.84 g of compound is obtained.

Melting point: 266° C.

EXAMPLE 9

Compound No. 15

5-(4-Amino-5-chloro-2-methoxyphenyl)-3-(8-azabicyclo[3.2.1]oct-3-yl)-1,3,4-oxadiazol-2(3H)-one hydrobromide 9.1. Phenylmethyl [2-chloro-4-[4-(8-azabicyclo[3.2.1]oct-3-yl)-5-oxo-4,5-dihydro-1,3,4-oxadiazol-2-yl]-5-methoxyphenyl]carbamate 5.78 g (15 mmol) of phenylmethyl [2-chloro-5-methoxy-4,5-dihydro-1,3,4-oxadiazol-2-yl)phenyl]carbamate, 6.0 g (23 mmol) of triphenylphosphine and 3.5 g (15 mmol) of 8-[(1,1-dimethylethoxy)carbonyl]-8-azabicyclo[3.2.1octan-3-ol dissolved in 50 ml of tetrahydrofuran are introduced into a 100 ml three-necked round-bottomed flask, the solution is cooled to 0° C. and 3.64 ml of ethyl azadicarboxylate are added dropwise. The mixture is allowed to return to 20° C. and is stirred for 3 h. The solvent is evaporated off under reduced pressure, the residue is taken up in 50 ml of dichloromethane, 25 ml of trifluoroacetic acid are added at 0° C., and the solution obtained is stirred at room temperature for 4 h.

The solvent is evaporated off under reduced pressure, 50 ml of water and 100 ml of diethyl ether are added and the precipitate is collected by filtration, rinsed with diethyl ether and dried.

5.0 g of white solid are obtained.

Melting point: 156–157° C.

9.2. 5-(4-Amino-5-chloro-2-methoxyphenyl)-3-(8-azabicyclo[3.2.1]oct-3-yl)-1,3,4-oxadiazol-2(3H)-one hydrobromide 5.0 g (10.6 xmol) of phenylmethyl [2-chloro-4-[4-(8-azabicyclo[3.2.1]oct-3-yl)-5-oxo-4,5-dihydro-1,3,4-oxadiazol-2-yl]-5-methoxyphenyl]carbamate dissolved in 10 ml of 33% hydrobromic acid in acetic acid are placed in a 25 ml round-bottomed flask and the mixture is stirred at room temperature for 24 h.

Diethyl ether is added and the precipitate is collected by filtration and rinsed several times with ether. 4.2 g of compound are obtained.

Melting point: 235–237° C.

EXAMPLE 10

Compound No. 13

5-(4-Amino-5-chloro-2-methoxyphenyl)-3-[8-[1-[5-[4-(dimethylamino)piperidin-1-yl]-5-oxopentyl]-8-azabicyclo[3.2.1]oct-3-yl]-1,3,4-oxadiazol-2(3H)-one(−)-bistartrate 0.5 g (1.16 mmol) of 5-(4-amino-5-chloro-2-methoxyphenyl)-3-(8-azabicyclo[3.2.1]oct-3-yl)-1,3,4oxadiazol-2(3H)-one hydrobromide, 0.286 g (1.16 mmol) of 1-(5-chloro-1-oxopentyl)-N,N-dimethylpiperidin-4-amine and 0.484 ml (3.48 mmol) of triethylamine dissolved in 10 ml of N,N-dimethylformamide are introduced into a 25 ml three-necked round-bottomed flask and the mixture is refluxed for 18 h.

The solvent is evaporated off under reduced pressure, water is added and the mixture is extracted with dichloromethane. The solvent is evaporated off under reduced pressure and the residue is purified by chromatography on a column of silica gel, eluting first with a 90/10 mixture of dichloromethane and methanol and then with an 80/20/2 mixture of dichloromethane, methanol and aqueous ammonia. An oil is obtained which is treated with two equivalents of tartaric acid and 0.35 g of white solid is finally isolated.

Melting point: 198–201° C.

The table which follows illustrates the chemical structures and the physical properties of a few compounds according to the invention.

TABLE (I)

| No. | $OR_1$ | $X_1$ | $X_2$ | $X_3$ | $R_2$ | Salt | m.p. (° C.) |
|---|---|---|---|---|---|---|---|
| 1 | $OCH_3$ | H | $NH_2$ | Cl | $-CH_3$ | — | 208 |
| 2 | $-O(CH_2)_2O-$ | $NH_2$ | Cl | | $-CH_2C_6H_5$ | — | 185 |
| 3 | $-O(CH_2)_2O-$ | $NH_2$ | Cl | | H | HCl | 210 |
| 4 | $-O(CH_2)_2O-$ | $NH_2$ | Cl | | $-CH_2CH_2C_6H_5$ | — | 227 |
| 5 | $-O(CH_2)_2O-$ | $NH_2$ | Cl | | $-CH_2CH_2CH_2CH_3$ | HBr | >260 |
| 6 | $-O(CH_2)_2O-$ | $NH_2$ | Cl | | $-CH(CH_3)_2$ | — | 254 |
| 7 | $-O(CH_2)_3-$ | H | Cl | | H | HCl | 254 |
| 8 | $-O(CH_2)_3-$ | H | Cl | | $-CH_2CH_2C_6H_5$ | HCl | 261 |
| 9 | $-O(CH_2)_3-$ | H | Cl | | $-CH_2CH_2CH_2CH_3$ | HCl | 242 |
| 10 | $-O(CH_2)_2-$ | H | Cl | | H | HCl | >260 |
| 11 | $-O(CH_2)_2-$ | H | Cl | | $-CH_2CH_2C_6H_5$ | HCl | 266 |
| 12 | $-O(CH_2)_2-$ | H | Cl | | $-CH_2CH_2CH_2CH_3$ | HCl | 238 |
| 13 | $-OCH_3$ | H | $NH_2$ | Cl | * | tar | 198–201 |
| 14 | $-OCH_3$ | H | $NH_2$ | Cl | $-CH_2CH_2CH_2CH_3$ | — | 166 |
| 15 | $-OCH_3$ | H | $NH_2$ | Cl | H | HBr | 235–237 |

In the Salt column, - denotes a compound in the form of a base, HCl denotes a hydrochloride, HBr denotes a hydrobromide and tar denotes a tartrate.

* In Compound No. 13, $R_2$ is a 5-[4-(dimethylamino)-1piperidyl]-5-oxopentyl group.

The compounds of the invention underwent tests which demonstrated their value as therapeutically active substances.

Thus, the compounds of the invention were studied as regards their affinity towards the $5-HT_4$ receptors in guinea pig striatum, according to the method described by Grossman et al. in *Br. J. Pharmacol.* (1993) 109 618–624.

Guinea pigs (Hartley, Charles River, France) weighing 300 to 400 g are sacrificed, their brains are removed and the striata are excized and frozen at −80° C.

On the day of the experiment the tissue is thawed to +4° C. in 33 volumes of HEPES-NaOH buffer (50 mM, pH=7.4 at 20° C.), the mixture is homogenized using a Polytron™ grinder, the homogenate is centrifuged at 48,000×g for 10 min, the pellet is recovered and resuspended, the suspension is recentrifuged in the same way and the final pellet is resuspended in HEPES-NaOH buffer in a proportion of 30 mg of tissue per ml. 100 μl of this membrane suspension are incubated at 0° C. for 120 min in the presence of [$^3$H] GR113808 (ligand described in the article mentioned, specific activity 80–85 Ci/mmol) in a final volume of 1 ml of HEPES-NaOH buffer (50 mM, pH=7.4), in the presence or absence of test compound. The incubation is stopped by filtration through a Whatman GF/B filter pretreated with 0.1% polyethyleneimine, each tube is rinsed with 4 ml of buffer at 0° C., a further filtration is carried out and the radioactivity retained on the filter is measured by liquid scintigraphy.

The non-specific binding is determined in the presence of 30 μM serotonin. The specific binding represents 90% of the total radioactivity recovered on the filter.

For each concentration of test compound, the percentage of inhibition of the specific binding of [$^3$H]GR113808 is determined, followed by the $IC_{50}$, the concentration of test compound which inhibits the specific binding by 50%.

The $IC_{50}$ values of the most active compounds are between 1.3 and 340 nM.

The compounds of the invention were also studied as regards their agonist or antagonist effects towards the 5-$HT_4$ receptors in rat oesophagus, according to the method described by Baxter et al. in *Naunyn Schmied. Arch. Pharmacol.* (1991) 343 439.

Male Sprague-Dawley rats weighing 300 to 450 g are used. A fragment of about 1.5 cm of the end part of the oesophagus is removed rapidly, the muscle layer is removed, and the internal muscular mucous tunic is opened longitudinally, mounted in an insulated-organ tank containing Krebs-Henseleit solution at 32° C. oxygenated by a stream of carbogen (95% O2 and 5% $CO_2$), and connected to an isometric transducer under a basal tension of 0.5 g. A contraction of the tissue is induced by addition of 0.5 $\mu M$ carbachol and, after waiting for the contraction to stabilize (15 min), the preparation is then exposed to serotonin (1 $\mu M$) in order to quantify the maximum relaxation. The tissue is washed and, after 20 min, a further 0.5 $\mu M$ carbachol is added and the preparation is exposed to the test compound, in increasing cumulative concentrations from 0.1 to 1 $\mu M$. The compounds which induce a relaxation re considered as 5-$HT_4$ agonists.

For compounds which do not induce relaxation, the preparation is exposed to serotonin in increasing cumulative concentrations, from 0.1 nM to a concentration which induces maximum relaxation, and the curve of relaxation due to serotonin, in the presence of the test compound, is then compared with a standard curve determined in the absence of the said compound. If its presence induces a shift of the curve towards the right, the test compound is considered as a 5-$HT_4$ antagonist.

The results of these two biological tests show that the compounds of the invention are powerful ligands of serotoninergic receptors of 5-$HT_4$ type, and that they act on these receptors either as agonists or as antagonists.

Lastly, the compounds of the invention underwent an in vitro study regarding their affinity for the histaminergic $H_3$ receptors of rat brain, essentially as described by Korte A. et al., *Biochem. Phys. Res. Commun.* (1990) 160 979–986, and West R. E. et al., *Mol. Pharmacol.* (1990) 38 610–613.

Male Sprague Dawley rats (OFA, Iffa Credo, France) weighing 250 to 300 g are sacrificed and their brains are removed. The tissues are homogenized using a Polytron™ grinder (position 7 for 20 sec) in 20 volumes of Tris-HCl buffer (50 mM, pH 7.4 at 22° C.). The homogenate is centrifuged at 1000×g for 10 min and the supernatant is then recentrifuged at 45,000×g for 20 min at 4° C. The pellet is then washed by resuspending it in the buffer and homogenizing and centrifuging it. The final pellet is resuspended in the buffer in a proportion of 100 mg of initial tissue per milliliter, and is then divided into 11 ml aliquot fractions, which are frozen at −80° C. On the day of the experiment, the membrane suspension (100 $\mu l$, 300 to 400 $\mu g$ of proteins) is incubated at 30° C. for 60 min in the presence of 0.5 nM [$^3$H]N$^\alpha$-methylhistamine (specific activity 75 to 80 Ci/mmol, New England Nuclear, Du Pont de Nemours, Boston, USA) in a final volume of 500 $\mu l$ of Tris-HCl buffer, in the presence or absence of test compound. The incubation is stopped by filtration through Whatman GF/B™ filters pretreated with polyethyleneimine (0.4%). Each reaction tube is rinsed three times with 4 ml of cold (0° C.) Tris-HCl buffer. The filters are dried in an oven at 120° C. for 5 min. The radioactivity retained on the filters is determined by liquid scintigraphy. The non-specific binding is determined in the presence of 10 $\mu M$ thioperamide (N-cyclohexyl-4-(1H-imidazol-4-yl)piperidine-1-carbothioamide).

For each concentration of test compound, the percentage inhibition of the specific binding of [$^3$H]N$^\alpha$-methylhistamine is calculated, after which the $IC_{50}$ concentration of compound which inhibits the binding by 50% is determined.

The compounds of the invention which are most active in this test have an $IC_{50}$ value of about 35 nM.

The results of the various biological tests carried out on the compounds of the invention show that they are ligands of the 5-HT, receptors and/or of the $H_3$ receptors.

These results suggest that the compounds can be used for the treatment and prevention of disorders in which the 5-$HT_4$ and/or $H_3$ receptors are involved, in particular as regards the central nervous system, the gastrointestinal system, the lower urinary apparatus system or the cardiovascular system.

As regards the central nervous system, these disorders and complaints especially include neurological and psychiatric disorders such as cognitive disorders, psychoses, compulsive and obsessive behavioral patterns and states of depression and anxiety. The cognitive disorders include, for example, deficiencies in memory and attention, states of dementia (senile dementias such as Alzheimer's disease or age-related dementias), cerebralvascular deficiencies and Parkinson's disease. The psychoses include, for example, paranoia, schizophrenia, mania and autism. The compulsive and obsessive behavioral patterns include, for example, eating disorders such as bulimia or loss of appetite. The states of depression and anxiety include, for example, anxieties of anticipational type (before a surgical operation, before dental treatment, etc.) and anxiety caused by dependence on or withdrawal from alcohol or drugs. Lastly, mention may also be made of mania, epilepsy, sleeping disorders, seasonal affective disorders and migraine.

As regards the gastrointestinal system, these disorders and complaints include, inter alia, direct or indirect disorders of gastromotility of the oesophagus, of the stomach or of the intestine, nausea, specific illnesses such as dyspepsia, ulcers, gastro-oesophageal reflux, flatulence, irritable bowel syndrome, intestinal secretion disorders, diarrhoea, for example that induced by cholera or by carcinoid syndrome, and disorders which may or may not be associated with atmospheric pollution, such as asthma, rhinitis and breathing difficulties.

As regards the lower urinary apparatus system, these disorders and complaints especially include urinary incontinence, dysuria and urine retention.

As regards the cardiovascular system, these disorders and complaints especially include pathologies associated, directly or indirectly, with cardiac arrhythmia, with hypertension, with ischaemia, with myocardial infarction or with unstable angina, problems of reocclusion after recanalization, for example after fibrinolytic or thrombolytic therapy, angioplasty or heart surgery. Glaucoma is also a disorder which can be treated by the compounds of the invention.

The compounds of the invention can be presented in all forms of compositions suitable for enteral or parenteral administration, such as tablets, sugar-coated tablets, gelatin capsules, wafer capsules, drinkable or injectable suspensions or solutions such as syrups or vials, etc., combined with suitable excipients and dosed to allow a daily administration of from 0.001 to 20 mg/kg.

What is claimed is:

1. Compound, in the form of a pure geometrical or optical isomer or a mixture of isomers, corresponding to the general formula (I)

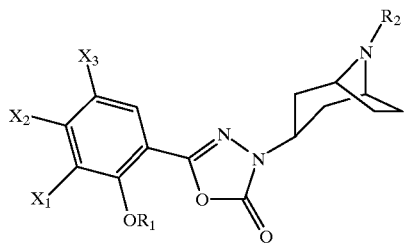

in which

R$_1$ represents a (C$_1$–C$_4$)alkyl or (C$_3$–C$_7$)cycloalkylmethyl group,

X$_1$ represents a hydrogen or halogen atom or a (C$_1$–C$_4$) alkoxy group, or alternatively OR$_1$ and X$_1$ together represent a group of formula —CH$_2$—, —O(CH$_2$)$_2$—, —O(CH$_2$)$_3$—, —O(CH$_2$)$_2$O— or —(CH$_2$)$_3$O—, X$_2$ represents a hydrogen atom or an amino group, X$_3$ represents a hydrogen or halogen atom, and R$_2$ represents a hydrogen atom, (C$_1$–C$_6$)alkyl group, a phenyl(C$_1$–C$_4$)alkyl group, or a group of general formula —(CH$_2$)$_n$CO—Z in which n represents a number from 1 to 6 and Z represents a 1-piperidyl or 4-(dimethylamino)-1-piperidyl group, in the form of the free base or of a pharmaceutically acceptable addition with an acid.

2. Compound according to claim 1, characterized in that R$_2$ represents a butyl group.

3. Compound according to claim 1, characterized in that R$_2$ represents a 2-phenylethyl.

4. Compound according to claim 1, characterized in that R$_2$ represents a 4-[4-(dimethylamino)-1-piperidyl]-4-oxobutyl group, a 5-[4-(dimethylamino)-1-piperidyl]-5-oxopentyl group or a 6-[4-(dimethylamino)-1-piperidyl]-6-oxohexyl group.

5. Process for the preparation of compounds according to claim 1, characterized in that an ester of general formula (II)

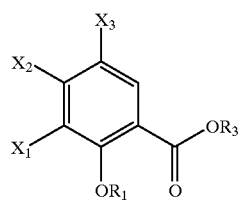

in which R$_1$, X$_1$, X$_2$ and X$_3$ are as defined in claim 1 and R$_3$ represents a methyl or ethyl group, is reacted with hydrazine hydrate, in order to obtain a hydrazide of general formula (III)

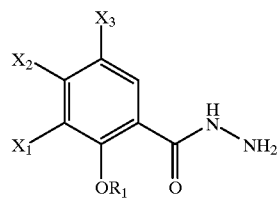

which is cyclized into the oxadiazole of general formula (IV)

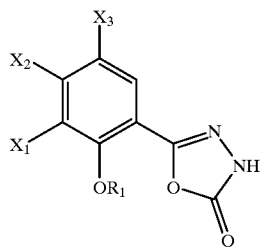

either by means of phosgene or by means of phenyl chloroformate, after which the oxadiazole of general formula (IV) is reacted with a tropanol of general formula (V)

in which R$_2$ is as defined with respect to the general formula (I), but is other than a hydrogen atom, or alternatively represents a (1,1-dimethylethoxy)carbonyl protecting group, in the presence of triphenylphosphine and ethyl azodicarboxylate, after which, if necessary, the nitrogen of the tropane ring is deprotected by means of trifluoroacetic acid in order to obtain a compound of general formula (I) in which R$_2$ represents a hydrogen atom, and, if so desired, the compound obtained is reacted with a derivative of general formula R$_2$—X, in which X represents a leaving group and R$_2$ is as defined with respect to the general formula (I), but is other than a hydrogen atom.

6. Pharmaceutical composition, characterized in that it contains a compound according to one of claims 1 to 4, combined with an excipient.

7. A method for treating or preventing an amenable disorder in which 5-HT$_4$ and/or H$_3$ receptors are involved which comprises administering an effective amount of a pharmacologically acceptable compound according to claim 1 to a patient in need of such therapy.

8. A method for treating or preventing an amenable disorder in which 5-HT$_4$ and/or H$_3$ receptors are involved which comprises administering an effective amount of a pharmacologically acceptable compound according to claim 2 to a patient in need of such therapy.

9. A method for treating or preventing an amenable disorder in which 5-HT$_4$ and/or H$_3$ receptors are involved which comprises administering an effective amount of a pharmacologically acceptable compound according to claim 3 to a patient in need of such therapy.

10. A method for treating or preventing an amenable disorder in which 5-$HT_4$ and/or $H_3$ receptors are involved which comprises administering an effective amount of a pharmacologically acceptable compound according to claim 4 to a patient in need of such therapy.

* * * * *